United States Patent
Higuchi et al.

(10) Patent No.: US 9,968,566 B2
(45) Date of Patent: May 15, 2018

(54) PHARMACEUTICAL COMPOSITION FOR PROPHYLAXIS AND/OR TREATMENT OF CORNEAL AND CONJUNCTIVAL DISEASES OR PRESBYOPIA CONTAINING STILBENE COMPOUND AS ACTIVE INGREDIENT

(71) Applicant: KEIO UNIVERSITY, Tokyo (JP)

(72) Inventors: Akihiro Higuchi, Tokyo (JP); Kazuo Tsubota, Tokyo (JP); Kiyoshi Fukuhara, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 0 days. days.

(21) Appl. No.: 15/506,893

(22) PCT Filed: Aug. 26, 2015

(86) PCT No.: PCT/JP2015/074052
§ 371 (c)(1),
(2) Date: Feb. 27, 2017

(87) PCT Pub. No.: WO2016/031869
PCT Pub. Date: Mar. 3, 2016

(65) Prior Publication Data
US 2017/0246122 A1 Aug. 31, 2017

(30) Foreign Application Priority Data
Aug. 28, 2014 (JP) .................................. 2014-174332

(51) Int. Cl.
*A61K 31/05* (2006.01)

(52) U.S. Cl.
CPC .................... *A61K 31/05* (2013.01)

(58) Field of Classification Search
CPC ..................................................... A61K 31/05
See application file for complete search history.

(56) References Cited

U.S. PATENT DOCUMENTS

2006/0111318 A1 5/2006 Okamoto
2016/0000809 A1 1/2016 Lee et al.

FOREIGN PATENT DOCUMENTS

JP 2006-298876 A 11/2006
JP 2008-110962 A 5/2008
(Continued)

OTHER PUBLICATIONS

Baskin et al., "Identification of novel SAR properties of the Jak2 small molecule inhibitor G6: Significance of the para-hydroxyl orientation," *Bioorganic & Medicinal Chemistry Letters*, 22: 1402-1407 (2012).
(Continued)

*Primary Examiner* — San Ming R Hui
(74) *Attorney, Agent, or Firm* — Leydig, Voit & Mayer, Ltd.

(57) ABSTRACT

A pharmaceutical composition for prophylaxis and/or treatment of a corneal and conjunctival disease or presbyopia, the composition containing a compound represented by Formula (I), or a salt thereof or a prodrug thereof as an active ingredient,

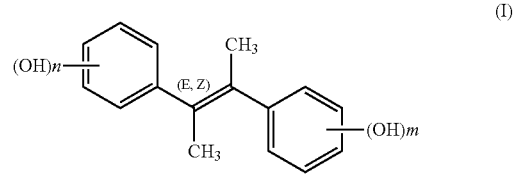

wherein m and n are each independently an integer of 0 to 5; m+n≥1; and each aromatic ring of the compound represented by Formula (I) may be substituted.

12 Claims, 5 Drawing Sheets

(56) References Cited

FOREIGN PATENT DOCUMENTS

| WO | WO 2007/020673 A1 | 2/2007 |
| WO | WO 2013/100660 A2 | 7/2013 |

OTHER PUBLICATIONS

Fukuhura et al., "Effect of Methyl Substitution on the Antioxidative Property and Genotoxicity of Resveratrol," *Chem. Res. Toxicol.*, 21(2): 282-287 (2008).
Imai et al., "Synthesis and radical-scavenging activity of a dimethyl catechin analogue," *Bioorganic & Medicinal Chemistry Letters*, 24: 2582-2584 (2014).
Patel et al., "Protein Kinase C δ (PKCδ) Splice Variants Modulate Apoptosis Pathway in 3T3L1 Cells during Adipogenesis," *The Journal of Biological Chemistry*, 288(37): 26834-26846 (2013).
Schneider et al., "Mammary Tumor Inhibiting Effect of 3,3'-Diacetoxy-α,β-dialkylstilbenes and of Related Stilbene Oxides," *Journal of Med. Chem.*, 25(2): 141-145 (1982).
Japanese Patent Office, International Search Report in International Patent Application No. PCT/JP2015/074052 (dated Oct. 6, 2015).

A

B

PHARMACEUTICAL COMPOSITION FOR PROPHYLAXIS AND/OR TREATMENT OF CORNEAL AND CONJUNCTIVAL DISEASES OR PRESBYOPIA CONTAINING STILBENE COMPOUND AS ACTIVE INGREDIENT

CROSS-REFERENCE TO RELATED APPLICATIONS

This patent application is the U.S. national phase of International Patent Application No. PCT/JP2015/074052, filed Aug. 26, 2015, which claims the benefit of Japanese Patent Application No. 2014-174332, filed on Aug. 28, 2014, which are incorporated by reference in their entireties herein.

TECHNICAL FIELD

CROSS REFERENCE OF RELATED APPLICATION

This application claims priority to Japanese Patent Application No. 2014-174332, filed Aug. 28, 2014, the disclosure of which is incorporated herein by reference in its entirety.

TECHNICAL FIELD

The present invention relates to a pharmaceutical composition for prophylaxis and/or treatment of corneal and conjunctival diseases or presbyopia containing a stilbene compound.

BACKGROUND ART

Resveratrol (trans-1,2-(3,4',5-trihydroxydiphenyl)ethylene) is a type of stilbenoid polyphenol, which is known for effects, for example, on life extension, prophylaxis of cardiovascular-associated diseases, and improvement in brain functions; and more reports have been made recently about an association with ocular diseases. For example, Patent Literature 1 reports that trans-stilbene derivatives, such as resveratrol or piceatannol, as a sirtuin activator are effective as a therapeutic agent for various ocular diseases, such as asthenopia.

CITATION LIST

Patent Literature

PTL 1: US2006/0111318

SUMMARY OF INVENTION

Technical Problem

However, the fact that the known stilbenoid polyphenol derivatives above are effective in the prophylaxis and/or treatment of a specific ocular disease was unknown.

An object of the present invention is to provide a novel stilbene compound effective in the prophylaxis and/or treatment of corneal and conjunctival diseases or presbyopia.

Another object of the present invention is to provide a novel stilbene compound having a strong antioxidant effect.

Solution to Problem

In an attempt to achieve the above objects, the present inventors found that a derivative in which two methyl groups are introduced into a vinyl group of a stilbene skeleton has stabilized activity and is effective in the prophylaxis and/or treatment of corneal and conjunctival diseases including dry eye, as well as presbyopia (aging of eyes). Based on such unexpected effects, the present invention has been accomplished. This novel stilbene derivative has a stronger antioxidant effect, compared to resveratrol.

The present invention is more specifically described below.

Item 1. A pharmaceutical composition for prophylaxis and/or treatment of a corneal and conjunctival disease or presbyopia, the composition containing a compound represented by Formula (I), or a salt thereof or a prodrug thereof as an active ingredient,

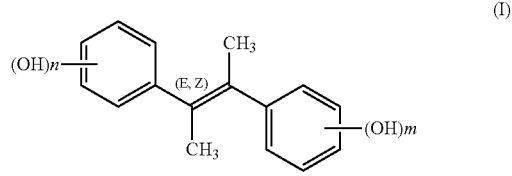

wherein m and n are each independently an integer of 0 to 5; m+n≥1; and each aromatic ring of the compound represented by Formula (I) may be substituted.

Item 2. The pharmaceutical composition according to Item 1, wherein m and n are each independently an integer of 1 to 3.

Item 3. The pharmaceutical composition according to Item 2, wherein the compound is a compound represented by Formula (II), or a salt thereof or a prodrug thereof,

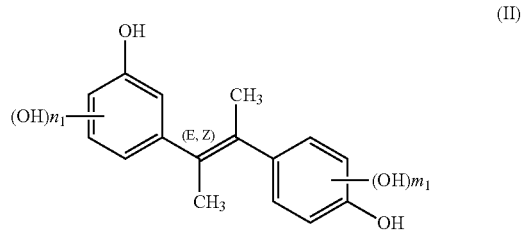

wherein $m_1$ and $n_1$ are each independently an integer of 0 to 2.

Item 4. The pharmaceutical composition according to Item 3, wherein the compound is a compound represented by Formula (III), or a salt thereof or a prodrug thereof,

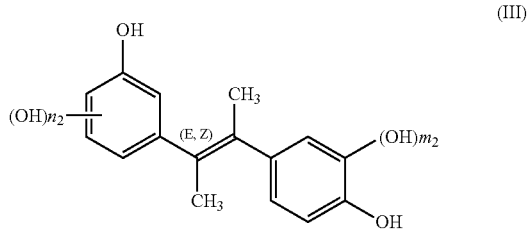

wherein $m_2$ is 0 or 1, and $n_2$ is an integer of 0 to 2.

Item 5. A prophylactic and/or therapeutic agent for a corneal and conjunctival disease or presbyopia, the agent containing a compound represented by Formula (I), or a salt thereof or a prodrug thereof as an active ingredient,

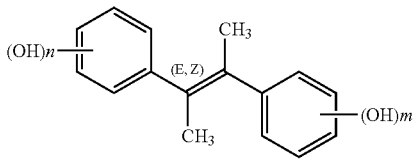

wherein m and n are each independently an integer of 0 to 5; m+n≥1; and each aromatic ring of the compound represented by Formula (I) may be substituted.

Item 6. A compound represented by Formula (I), or a salt thereof or a prodrug thereof for use in the prophylaxis and/or treatment of a corneal and conjunctival disease or presbyopia,

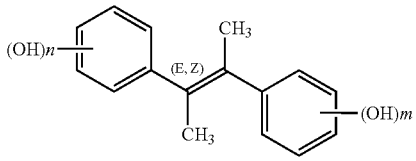

wherein m and n are each independently an integer of 0 to 5; m+n≥1; and each aromatic ring of the compound represented by Formula (I) may be substituted.

Item 7. A method for preventing and/or treating a corneal and conjunctival disease or presbyopia, the method comprising administering to a patient an effective amount of a compound represented by Formula (I), or a salt thereof or a prodrug thereof,

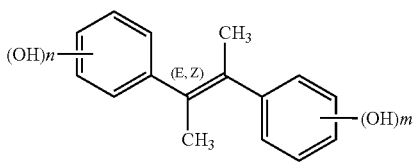

wherein m and n are each independently an integer of 0 to 5; m+n≥1; and each aromatic ring of the compound represented by Formula (I) may be substituted.

Advantageous Effects of Invention

According to the present invention, the compound of the present invention or a salt thereof is useful for prophylaxis and/or treatment of a corneal and conjunctival disease or presbyopia. The compound of the present invention or a salt thereof is also useful as an antioxidant agent.

DESCRIPTION OF EMBODIMENTS

Figure 1:
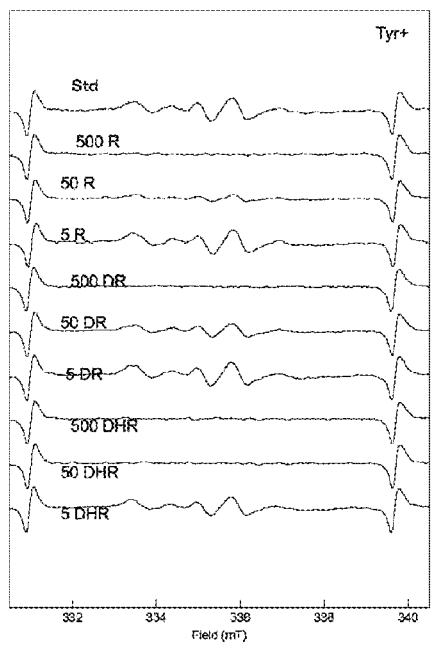
FIG. 1 is graphs showing measurement results of electron spin resonance (ESR). (A): Amount of tyrosine radical; and (B): Amount of hydroxyl radical. In the graphs, "5," "50," and "500" respectively represent 5 µM, 50 µM, and 500 µM; and "R," "DR," and "DHR" respectively refer to resveratrol, dimethyl resveratrol (Formula (V)), and dimethylhydroxy resveratrol (Formula (VI)). Std: standard substance.
Figure 1:
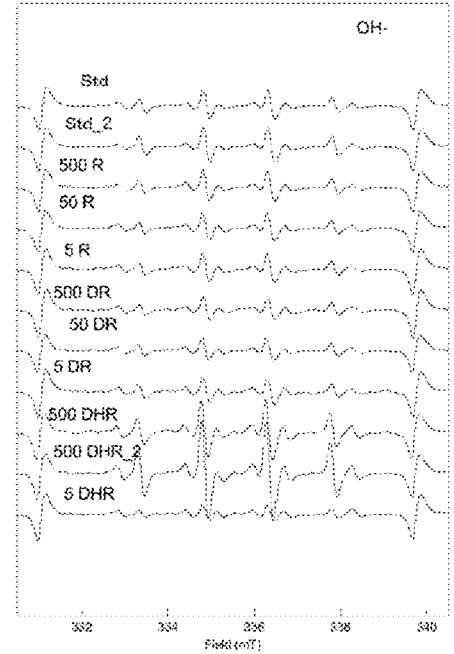

As used herein, the term "treating" or "treatment" refers to healing or improvement of a disease or a symptom, or suppression of a symptom, and the term also means "prophylaxis." The term "prophylaxis" refers to prevention of the onset of a disease or symptom.

The compound of the present invention includes the compound represented by the following Formula (I).

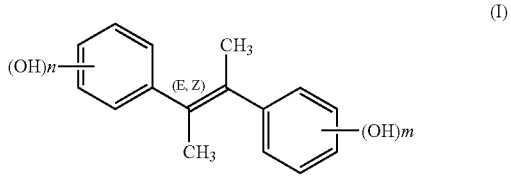

In the formula, m and n each independently represent an integer of 0 to 5, and m+n≥1. However, 4-[3-(4-hydroxyphenyl)but-2-en-2-yl]benzene-1,2-diol of the following Chemical Formula (i) is excluded from the compounds of the present invention.

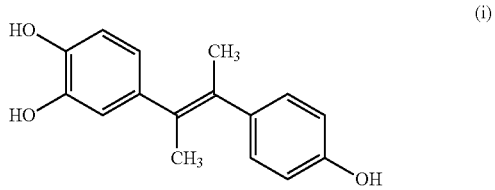 [SMILES: C/C(=C(/C)c1ccc(O)c(O)c1)c1ccc(O)cc1]

Each aromatic ring in the compound represented by Formula (I) may be substituted with, for example, lower alkyl having 1 to 6 carbon atoms (e.g., methyl, ethyl, n-propyl, isopropyl, butyl, isobutyl, sec-butyl, tert-butyl, cyclopropyl, and cyclobutyl), lower alkoxy having 1 to 6 carbon atoms (e.g., methoxy, ethoxy, propoxy, and isopropoxy), and halogen (e.g., fluorine, chlorine, and bromine).

In the compound represented by Formula (I) above, the trans (F) form and cis (Z) form exist in the vinyl group of the stilbene skeleton. The compounds may be in either the trans or cis form, or in a combination of these forms. The compound represented by Formula (I) is preferably in the trans form. Hereinafter, the compounds in trans form and cis form are both encompassed by the compounds of the present invention, unless otherwise specified.

Among the compounds represented by Formula (I), specific compounds may exist in stereoisomeric forms. In addition, the present invention encompasses all the compounds including cis- and trans-isomers, R- and S-enantiomers, diastereomers, (D)-isomers, (L)-isomers, racemic mixtures thereof, and other mixtures thereof. Additional asymmetric carbon atoms may also be present in a substituent, such as alkyl. All such isomers, as well as mixtures thereof, are encompassed by the compounds of the present invention.

The hydroxyl groups in the aromatic rings may be in the ortho-, meta-, or para-position. Past studies of the present inventors have confirmed the activity relevant to corneal and conjunctival diseases, presbyopia, or anti-oxidization, regardless of these positions.

As the number of hydroxyl groups on the aromatic rings increases, the activity relevant to corneal and conjunctival diseases, presbyopia, or anti-oxidization increases; however, the stability of the compound becomes poor. The present invention confirmed that the introduction of methyl groups into the vinyl group of a stilbene skeleton makes it possible to increase the activity while maintaining the stability of the compound. This is an effect of the present invention that cannot be expected.

In one embodiment, m and n are each independently an integer of 1 to 3. In another embodiment, m and n are each independently an integer of 1 to 3, and the total number of hydroxyl groups on the aromatic rings is 3 to 6.

In one embodiment, the compound above of the present invention is represented by the following formula (II).

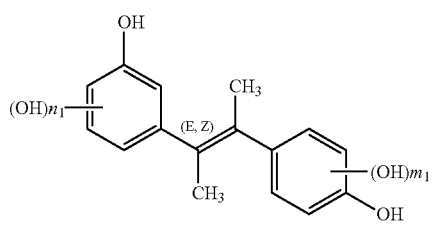

In the formula, $m_1$ and $n_1$ are each independently an integer of 0 to 2.

In one embodiment, the compound above of the present invention is represented by the following formula (III).

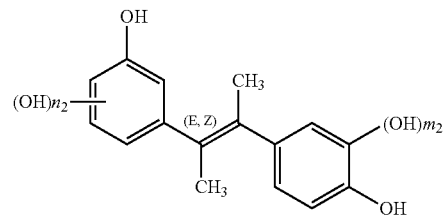

In the formula, $m_2$ is 0 or 1, and $n_2$ is an integer of 0 to 2.

In one embodiment, the compound above of the present invention is represented by the following formula (IV).

(IV)

In the formula, $m_3$ is 0 or 1, $n_3$ is 0 or 1, and the compound is in the trans form.

In one embodiment, the compound of the present invention is (E)-5-[3-(4-hydroxyphenyl) but-2-en-2-yl]benzene-1,3-diol represented by the following Formula (V) or (E)-4-[3-(3,5-dihydroxyphenyl)but-2-en-2-yl]benzene-1,2-diol represented by Formula (VI).

(V)

(VI)

The compound represented by Formula (I) of the present invention may form a salt. Examples of the salt include acid addition salts, such as inorganic acid salts (e.g., hydrochloride, sulfate, hydrobromide, and phosphate), organic acid salts (e.g., acetate, trifluoroacetate, succinate, maleate, fumarate, propionate, citrate, tartrate, lactate, oxalate, methanesulfonate, and p-toluenesulfonate), and the like.

Furthermore, the present invention also encompasses various hydrates, solvates, as well as polymorphic crystal substances of the compound represented by Formula (I) or a salt thereof.

The present invention may be a prodrug of the compound represented by Formula (I). A prodrug of the compound represented by Formula (I) refers to a compound that will be converted into a compound represented by Formula (I) by a reaction within the body.

Examples of the prodrugs of the compound represented by Formula (I) include compounds in which the hydroxyl groups of the compound represented by Formula (I) are acetylated, acylated alkylated, phosphated, sulfated, or borated. These compounds may be produced by known methods.

The prodrug of the compound represented by Formula (I) may be used as is, or in the form of a pharmacologically acceptable salt. Examples of such salts include salts with, for example, inorganic or organic bases when the prodrug of the compound represented by Formula (I) contains an acidic group, such as a carboxyl group; and salts with inorganic or organic acids when the prodrug of the compound represented by Formula (I) contains a basic group, such as an amino group. The prodrug of the compound represented by Formula (I) may take a hydrate form or a non-hydrate form.

The compound represented by Formula (I) may be produced, for example, by the following scheme.

added to the reaction mixture, chromate salts are removed by celite filtration, and then the filtrate is distilled off under reduced pressure. The residue is purified by column chromatography to obtain a compound of Formula (2).

Step (B)

Next, in an argon atmosphere, methyl bromide magnesium (MeMgBr) is added dropwise to a mixture of tetrabutyl ammonium chloride (Bu$_4$NCl) and diethylene glycol dimethyl ether (diglyme), followed by stirring. After the reaction mixture is cooled, a solution of the compound of Formula (2) in THF is added thereto dropwise, followed by further stirring. The reaction mixture is separated into layers, and the organic layer is dried. After the solvent is distilled off under reduced pressure, the residue is purified by column chromatography to obtain a compound of Formula (3)

Step (C)

Next, in an argon atmosphere, 4-N,N-dimethylaminopyridine (DMAP), N-ethyldiisopropylamine (i-Pr$_2$NEt), and trifluoroacetic anhydride (F$_3$CCO)$_2$O) are added to a solution of the compound of Formula (3) in methylene chloride, followed by stirring. The reaction mixture is separated into layers, and the organic layer is dried. The residue obtained by distilling off the solvent under reduced pressure is dis-

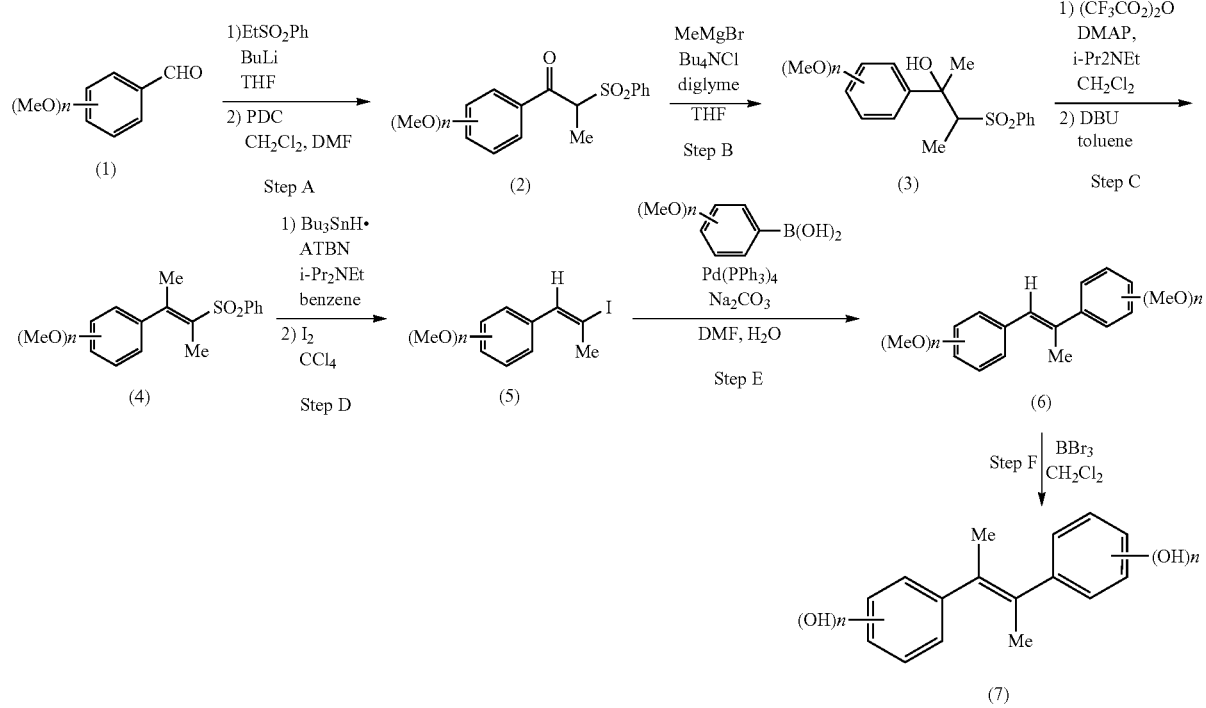

Step (A)

First, a solution of ethyl phenyl sulfone (EtSO$_2$Ph) in tetrahydrofuran (THF) is cooled, to which butyl lithium (BuLi) is added dropwise, and the resulting mixture is stirred. A THF solution of methoxybenzaldehyde (1) whose hydroxyl group on the aromatic ring is protected by a methyl group is added dropwise to the reaction mixture, followed by further stirring. The reaction mixture is separated into layers, and the organic layer is dried. After the solvent is distilled off under reduced pressure, the residue is dissolved in methylene chloride (CH$_2$Cl$_2$) and dimethyl formamide (DMF), to which molecular sieves and pyridinium dichromate (PDC) are further added, followed by stirring. Ethyl acetate is solved in anhydrous toluene, and then diazabicycloundecene (DBU) is added thereto in an argon atmosphere, followed by further stirring. The reaction mixture is separated into layers, and the organic layer is dried. The residue obtained by distilling off the solvent under reduced pressure is purified by column chromatography to obtain a compound of Formula (4).

Step (D)

Next, in an argon atmosphere, a benzene solution of the compound of Formula (4), hydrogenated tributyltin (Bu$_3$SnH), azobisisobutyronitrile (AIBN), and N-ethyl diisopropylamine is heated to reflux. The reaction mixture is separated into layers, and the organic layer is dried. The residue obtained by distilling off the solvent under reduced pressure is dissolved in carbon tetrachloride ($CCl_4$), and then, in an argon atmosphere, iodine is added thereto, followed by stirring. The reaction mixture is separated into layers, and the organic layer is distilled off under reduced pressure. The obtained residue is further separated into layers, and the organic layer is dried. The residue obtained by distilling off the solvent under reduced pressure is purified by column chromatography to obtain a compound of Formula (5)

Step (E)

Next, a suspension of the compound of Formula (5), methoxy (one or more methyl groups) phenylboronic acid, sodium carbonate, and distilled water in DMF is stirred. Then, $Pd(PPh_3)_4$ is added to the reaction mixture, followed by heating and stirring. The reaction mixture is separated into layers, and the organic layer is dried, followed by distilling off the solvent under reduced pressure. The residue is purified by column chromatography to obtain compounds of Formula (6) as a mixture of the cis and trans isomers. These cis and trans isomers may be separated by HPLC.

Step (F)

Next, in an argon atmosphere, boron tribromide ($BBr_3$) is added dropwise to a solution of the compound of Formula (6) (a mixture of the cis and trans isomers) in dehydrated methylene chloride. After the reaction mixture is stirred, the mixture is further stirred. The reaction mixture is separated into layers, and the water layer is further separated into layers with another solvent. After the obtained organic layer is dried, the solvent is distilled off under reduced pressure. The residue is roughly purified by column chromatography to obtain a compound of Formula (7) as a mixture.

By performing the above reactions, the compound of the present invention having one or more hydroxyl groups on the two aromatic rings and in which two methyl groups are introduced into the vinyl group of a stilbene skeleton is produced.

The compound of the present invention exhibits an excellent effect on prophylaxis and/or treatment of a corneal and conjunctival disease, and is thus useful as a prophylactic and/or therapeutic agent for a corneal and conjunctival disease. Further, a pharmaceutical composition for prophylaxis and/or treatment of a corneal and conjunctival disease, containing the compound of the present invention as an active ingredient, is also encompassed by the scope of the present invention. Corneal and conjunctival diseases include dry eye, keratoconjunctivitis sicca, superficial punctate keratopathy, corneal erosion, corneal ulcer, and the like.

In this specification, the expression "corneal and conjunctival" or "keratoconjunctival" means corneal and/or conjunctival, and the term "corneal and conjunctival disease" refers to a disease in cornea and/or conjunctiva. The diseases referred to in the present invention, such as dry eye, keratoconjunctivitis sicca, superficial punctate keratopathy, corneal erosion, and corneal ulcer, are generally encompassed by corneal and conjunctival diseases, but are not necessarily attributable to corneal and conjunctival diseases. Therefore, in the present invention, dry eye, keratoconjunctivitis sicca, superficial punctate keratopathy, corneal erosion, corneal ulcer, and the like also include those that are not attributable to corneal and conjunctival diseases.

Further, the compound of the present invention has an excellent effect on the prophylaxis and/or treatment of presbyopia, and is useful as a prophylactic and/or therapeutic agent for presbyopia. A pharmaceutical composition for prophylaxis and/or treatment of presbyopia, containing the compound of the present invention as an active ingredient, is also encompassed by the scope of the present invention.

Additionally, the compound of the present invention has an excellent antioxidant effect, and is also useful as an antioxidant agent.

The compound of the present invention can be used for patients, such as mammals including human (e.g., human, cow, horse, pig, monkey, dog, cat, mouse, rat, rabbit, goat, and sheep), and preferably human.

When the compound of the present invention is incorporated into a pharmaceutical composition, a pharmaceutically acceptable carrier may optionally be combined. Various dosage forms are possible according to the purpose of the prophylaxis or treatment. The forms are not particularly limited, and may be, for example, eye drops, oral preparations, injections, suppositories, ointments, patches, and the like, and preferably eye drops. These dosage forms may be produced by known preparation methods commonly used by a person skilled in the art. Eye drops may be any of aqueous eye drops, non-aqueous eye drops, suspended eye drops, emulsified eye drops, eye ointments, and the like. These formulations may be produced by preparation methods known to a person skilled in the art by optionally combining, as a composition suitable for the dosage form, a pharmaceutically acceptable carrier, such as a tonicity agent, a chelating agent, a stabilizer, a pH regulator, an antiseptic agent, an antioxidant agent, a solubilizing agent, and a thickening agent.

Examples of tonicity agents include saccharides such as glucose, trehalose, lactose, fructose, mannitol, xylitol, and sorbitol; polyhydric alcohols such as glycerin, polyethylene glycol, and propylene glycol; inorganic salts such as sodium chloride, potassium chloride, and calcium chloride; and the like. The amount thereof is preferably 0 to 5 wt % based on the total amount of the composition.

Examples of chelating agents include edetates such as disodium edetate, calcium disodium edetate, trisodium edetate, tetrasodium edetate, and calcium edetate, ethylenediamine tetraacetate, nitrilotriacetic acid or salts thereof, sodium hexametaphosphate, citric acid, and the like. The amount thereof is preferably 0 to 0.2 wt % based on the total amount of the composition.

Examples of stabilizers include sodium hydrogen sulfite and the like. The amount thereof is preferably 0 to 1 wt % based on the total amount of the composition.

Examples of pH regulators include acids (e.g., hydrochloric acid, carbonic acid, acetic acid, and citric acid) and bases (e.g., alkali metal hydroxides, such as sodium hydroxide and potassium hydroxide; alkali metal carbonates or hydrogen carbonates, such as sodium carbonate; alkali metal acetates, such as sodium acetate; alkali metal citrates such as sodium citrate; and trometamol). The amount thereof is preferably 0 to 20 wt % based on the total amount of the composition.

Examples of antiseptic agents include sorbic acid, potassium sorbate; parahydroxybenzoate esters, such as methyl parahydroxybenzoate, ethyl parahydroxybenzoate, propyl parahydroxybenzoate, and butyl parahydroxybenzoate; chlorexidine gluconate; quaternary ammonium salts, such as benzalkonium chloride, benzethonium chloride, and cetylpyridinium chloride; alkylpolyaminoethylglycine; chlorobutanol; Polyquad; polyhexamethylene biguanide; chlorhexidine; and the like. The amount thereof is preferably 0 to 0.2 wt % based on the total amount of the composition.

Examples of antioxidant agents include dry sodium sulfite, sodium pyrosulfite, concentrated mixed tocopherol, and the like. The amount thereof is preferably 0 to 0.4 wt % based on the total amount of the composition.

Examples of solubilizing agents include sodium benzoate, glycerin, polyvinyipyrrolidone, macrogol, D-mannitol, and the like. The amount thereof is preferably 0 to 3 wt % based on the total amount of the composition.

Examples of thickening agents include methylcellulose, ethylcellulose, carmellose sodium, xanthan gum, sodium chondroitin sulfate, hydroxyethylcellulose, hydroxypropylcellulose, hydroxypropylmethylcelluilose, polyvinylpyrrolidone, polyvinyl alcohol, and the like. The amount thereof is preferably 0 to 70 wt % based on the total amount of the composition.

An eye drop may be prepared by, for example, dissolving or suspending desired components mentioned above in an aqueous solvent, such as sterilized purified water or physiological saline, or a non-aqueous solvent, such as vegetable oil, i.e., cottonseed oil, soybean oil, sesame oil, or peanut oil, at a predetermined osmotic pressure, and subjecting the solution or suspension to sterilization treatment such as sterilization by filtration.

When an eye drop is prepared, an ointment base may be used in addition to the above-mentioned various components. The ointment base is not particularly limited. Preferable examples include oily bases, such as Vaseline, liquid paraffin, and polyethylene; emulsion bases in which the oil phase and the aqueous phase are emulsified with a surfactant or the like; water-soluble bases comprising hydroxypropylmethylcellulose, carboxymethylcellulose, polyethylene glycol, or the like; and the like.

The administration dose of the prophylaxis or therapeutic agent for a corneal and conjunctival disease and/or presbyopia of the present invention, or the antioxidant agent of the present invention varies depending on the patient's body weight, age, gender, symptoms, dosage form, number of doses, and the like. The compound of the present invention is usually administered in a daily dose of 0.1 to 1000 µg, and preferably 1 to 200 µg, per adult in a single dose or in several divided doses. For liquid eye drops, those with a concentration of 0.01 to 50 mg/mL, and preferably 0.1 to 10 mg/mL, may be administrated several times per day with one to several drops each time.

All of the patent applications and documents cited in this specification are incorporated herein by reference in their entirety.

The present invention is described below in more detail with reference to Examples. However, the present invention is not limited to these Examples.

EXAMPLES

Example 1

Production of the Compound of the Present Invention

Resveratrol was obtained from Sigma-Aldrich (product number: R5010-100MG). In accordance with the following scheme, (E)-5-[3-(4-hydroxyphenyl)but-2-en-2-yl]benzene-1,3-diol (DR, hereinbelow referred to as "dimethyl resveratrol"), which is a compound represented by Formula (V) of the present invention, and (E)-4-[3-(3,5-dihydroxyphenyl)but-2-en-2-yl]benzene-, 2-diol (DHR, hereinbelow referred to as "dimethylhydroxy resveratrol"), which is a compound represented by Formula (VI) of the present invention, were produced.

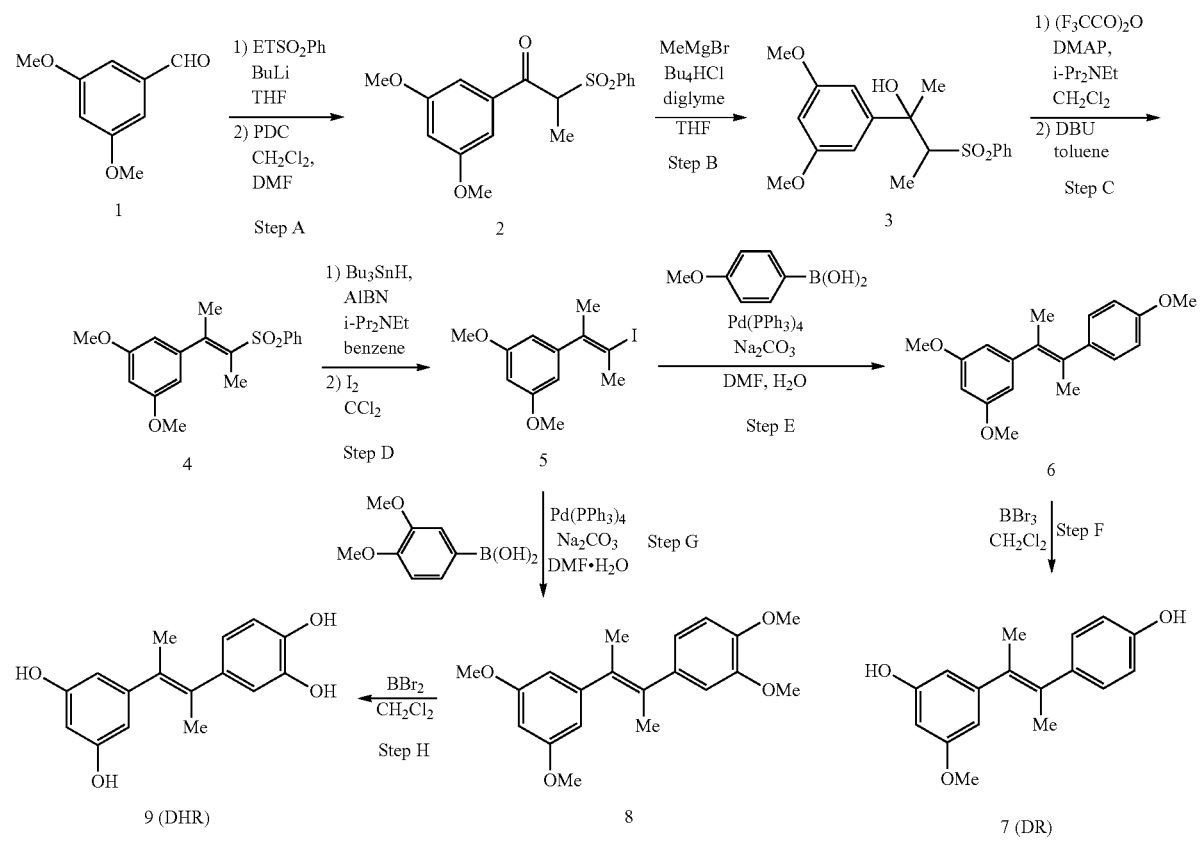

Step A: Production of 1-(3,5-dimethoxyphenyl)-2-(phenylsulfonyl)propan-1-one (2)

A solution of ethyl phenyl sulfone (EtSO$_2$Ph) (7.72 g, 45.1 mmol) in THF (60 mL) was cooled to −80° C., and butyl lithium (2.66 mol/L of n-hexane (hereinbelow simply referred to as "hexane") solution, 17.0 mL, 45.1 mmol) was added thereto dropwise, followed by stirring for 40 minutes. A solution of 3,5-dimethoxybenzaldehyde (1) (5.0 g, 30.09 mmol) in THF (30 mL) was added to the reaction mixture dropwise, followed by stirring for another 30 minutes. The reaction mixture was separated into layers using a saturated aqueous ammonium chloride solution and ethyl acetate, and the organic layer was dried over anhydrous sodium sulfate. After the solvent was distilled off under reduced pressure, the obtained residue was dissolved in methylene chloride (50 mL) and DMF (10 mL). Then, molecular sieves 4 Å (10 g) and PDC (56.6 g, 150.5 mmol) were further added thereto, followed by stirring at room temperature for 18 hours. After ethyl acetate (50 mL) was added to the reaction mixture, chromate salts were removed by celite filtration, and the filtrate was distilled off under reduced pressure. The residue was purified by column chromatography (silica gel, hexane/methylene chloride/ethyl acetate=20/20/1 (volume ratio)) to obtain Compound. 2 (8.16 g, 81%) as a white solid.
$^1$H NMR (400 MHz, CDCl$_3$) 0. 1.57 (d, J=7.2 Hz, 3H), 3.83 (s, 6H), 6.67-6.68 (m, 1H), 7.07 (d, J=2.0 Hz, 2H), 7.51-7.55 (m, 2H), 7.64-7.68 (m, 1H), 7.80-7.82 (m, 2H); $^{13}$C NMR (125 MHz, CDCl$_3$) 13.3, 55.6, 65.1, 106.4, 106.8, 128.9, 129.8, 134.2, 136.1, 138.0, 160.9; FAB-MS m/z 335 (M$^+$+H).

Step B: Production of 2-(3,5-dimethoxyphenyl)-3-(phenylsulfonyl)butan-2-ol (3)

Methyl bromide magnesium (1.0 mol/L THF solution, 9.0 mL, 9.0 mmol) was added dropwise at 0° C. in an argon atmosphere to a mixture of tetrabutyl ammonium chloride (167 mg, 0.6 mmol) and diethylene glycol dimethyl ether (1.28 mL, 9.0 mmol), followed by stirring for 30 minutes. After the reaction mixture was cooled to −40° C., a solution of Compound 2 (1.0 g, 3.0 mmol) in THF (15 mL) was added thereto dropwise, followed by stirring for another 25 hours. The reaction mixture was separated into layers using a saturated aqueous ammonium chloride solution and ethyl acetate, and the organic layer was dried over anhydrous sodium sulfate. After the solvent was distilled off under reduced pressure, the residue was purified by column chromatography (silica gel, hexane/methylene chloride/ethyl acetate=15/15/1 (volume ratio)) to obtain Compound 3 (661 mg, 63%) as a colorless syrupy substance.
$^1$H NMR (400 MHz, CDCl$_3$) 0.96 (d, J=7.2 Hz, 3H), 1.92 (s, 3H), 3.50 (q, J=7.2 Hz, 1H), 3.79 (s, 6H), 3.95 (s, 1H), 6.34 (t, J=2.4 Hz, 1H), 6.57 (d, J=2.4 Hz, 2H), 7.54-7.59 (m, 2H), 7.63-7.67 (m, 1H), 7.85-7.88 (m, 2H); $^{13}$C NMR (125 MHz, CDCl$_3$) 12.4, 30.8, 55.4, 67.7, 75.7, 98.7, 103.1128.3, 129.2, 133.8, 139.1, 148.0, 160.7; FAB-MS m/z 351 (M$^+$+H).

Step C: Production of (E)-1,3-dimethoxy-5-[3-(phenylsulfonyl) but-2-en-2-yl]benzene (4)

4-N,N-Dimethylaminopyridine (597 mg, 4.89 mmol), N-ethyldiisopropylamine (1.7 mL, 9.77 mmol), and trifluoroacetic anhydride (1.38 mL, 9.77 mmol) were added at 0° C. in an argon atmosphere to a solution of Compound 3 (1.71 g, 4.89 mmol) in methylene chloride (40 mL), followed by stirring at room temperature for 90 minutes. The reaction mixture was separated into layers using a saturated aqueous sodium hydrogen carbonate solution and methylene chloride, and the organic layer was dried over anhydrous sodium sulfate. After the residue obtained by distilling off the solvent under reduced pressure was dissolved in anhydrous toluene (40 mL), diazabicycloundecene (DBU) (2.92 mL, 19.5 mmol) was added at 0° C. in an argon atmosphere, followed by stirring at room temperature for another 80 minutes. The reaction mixture was separated into layers using 0.5N hydrochloric acid and ethyl acetate, and the organic layer was dried over anhydrous sodium sulfate. The residue obtained by distilling off the solvent under reduced pressure was purified by column chromatography (silica gel, hexane/ethyl acetate=3/1 (volume ratio)) to obtain Compound 4 (990 mg, 61%) as a white solid.
$^1$H NMR (400 MHz, CDCl$_3$) 1.6-1.87 (m, 3H), 2.44-2.45 (m, 3H), 3.77 (s, 6H), 6.19 (d, J=2.0 Hz, 2H), 6.38 (t, J=2.0 Hz, 1H), 7.55-7.59 (m, 2H), 7.62-7.64 (m, 1H), 7.94-7.96 (m, 2H); $^{13}$C NMR (125 MHz, CDCl$_3$) 17.7, 22.4, 55.4, 99.2, 104.5, 127.2, 129.1, 133.1, 133.7, 141.4, 144.9, 149.7, 161.0; FAB-MS m/z 333 (M$^+$+H)

Step D: Production of 1-(3-iodobut-2-en-2-yl)-3,5-dimethoxybenzene (5)

A solution of Compound 4 (580 mg, 1.75 mmol), hydrogenated tributyltin (1.41 mL, 5.24 mmol), azobisisobutyronitrile (AIBN) (143 mg, 0.87 mmol), and N-ethyldiisopropylamine (0.91 mL, 5.24 mmol) in benzene (17 mL) was heated to reflux in an argon atmosphere for 20 hours. The reaction mixture was separated into layers using a saturated aqueous sodium hydrogen carbonate solution and hexane, and the organic layer was dried over anhydrous sodium sulfate. After the residue obtained by distilling off the solvent under reduced pressure was dissolved in carbon tetrachloride (17 mL), iodine (1.77 g, 6.98 mmol) was added at 0° C. in an argon atmosphere, followed by stirring at room temperature for 90 minutes. The reaction mixture was separated into layers using a saturated aqueous sodium hydrogen carbonate solution (100 mL), a saturated aqueous sodium thiosulfate solution (100 mL), and methylene chloride, and the organic layer was distilled off under reduced pressure. The obtained residue was further separated into layers using a 10% aqueous potassium fluoride solution and methylene chloride, and the organic layer was dried over anhydrous sodium sulfate. The residue obtained by distilling off the solvent under reduced pressure was purified by column chromatography (silica gel, hexane/ethyl acetate=20/1 (volume ratio)) to obtain Compound 5 (533 mg, 96%, mixture of 2:1) as an oily substance. $^1$H NMR (400 MHz, CDCl$_3$) 2.07-2.08 (m, 1H), 2.21-2.22 (m, 2H), 2.42-2.43 (m, 2H), 2.63-2.64 (m, 1H), 3.78 (s, 4H), 3.80 (s, 2H), 6.27-6.28 (m, 2H), 6.36-6.38 (m, 1H); $^{13}$C NMR (125 MHz, CDCl$_3$) 20.5, 30.6, 31.7, 55.3, 94.5, 98.1, 98.8, 98.9, 105.7, 141.8, 142.1, 142.9, 150.3, 160.5, 160.6; FAB-MS m/z 319 (M$^+$+H).

Step E: Production of 1,3-dimethoxy-5-[3-(4-methoxyphenyl)but-2-en-2-yl]benzene) (6)

A suspension of Compound 5 (450 mg, 1.41 mmol), 4-methoxy phenylboronic acid (321 mg, 2.12 mmol), sodium carbonate (448 mg, 4.23 mmol), and distilled water (0.7 mL) in DMF (7 mL) was stirred at room temperature for 15 minutes. Then, Pd(PPh$_3$)$_4$ (163 mg, 0.14 mmol) was added to the reaction mixture, followed by stirring at 90° C. for 90 minutes. The reaction mixture was separated into layers using saturated saline and ethyl acetate, the organic layer was dried over anhydrous sodium sulfate, and the solvent was distilled off under reduced pressure. The residue was purified by column chromatography (silica gel, hexane/ethyl acetate=30/1 (volume ratio)) to obtain Compound 6 (316 mg, 75%, solid) as a mixture of 2:1. (E)-6 (Rt=5.6 min) and (Z)-6 (Rt=6.4 min) were separated under the following conditions and used as samples for instrumental analysis:

HPLC (column: SHIMADZ U Shim Pack PRC-SIL (250× 20 mm));

Measurement wavelength: 254 nm;

Mobile phase: hexane/ethyl acetate=30/1 (volume ratio); and

Flow rate: 20 mL/min.

(E)-6; $^1$H NMR (400 MHz, CDCl$_3$) 1.88 (s, 6H), 3.82 (s, 6H), 3.83 (s, 3H), 6.37 (t, 3=2.0 Hz, 1H), 6.41 (d, J=2.0 Hz, 2H), 6.89-6.93 (m, 2H), 7.18-7.21 (m, 2H); $^{13}$C NMR (125 MHz, CDCl$_3$) 22.4, 22.5, 55.2, 55.3, 98.2, 106.3, 113.5, 129.3, 132.4, 132.8, 136.5, 146.9, 158.0, 160.6; FAB-MS m/z 299 (M$^+$+H). (Z)-6; $^1$H NMR (400 MHz, CDCl$_3$) 2.13 (s, 6H), 3.58 (s, 6H), 3.72 (s, 3H), 6.13 (d, J=2.4 Hz, 2H), 6.16 (t, J==2.4 Hz, 1H), 6.64-6.66 (m, 2H), 6.90-6.93 (m, 2H); $^{13}$C NMR (125 MHz, CDCl$_3$) 21.3, 21.5, 55.1, 55.1, 98.0, 107.4, 113.0, 129.9, 132.2, 132.5, 137.1, 146.8, 157.5, 159.9; FAB-MS m/z 299 (M$^+$+H).

Step F: Production of (E)-5-[3-(4-hydroxyphenyl) but-2-en-2-yl]benzene-1,3-diol (7)

Boron tribromide (1.0 mol/L CH$_2$Cl$_2$ solution, 6.7 mL, 6.7 mmol) was added dropwise at −20° C. in an argon atmosphere to a solution of Compound 6 (mixture of 2:1, 400 mg, 1.34 mmol) in dehydrated methylene chloride (10 mL). After the reaction mixture was stirred at −20° C. for 95 minutes, the mixture was stirred at room temperature for another 95 minutes. The reaction mixture was separated into layers using distilled water and methylene chloride, and the water layer was further separated into layers using ethyl acetate. After the obtained organic layers were dried over anhydrous sodium sulfate, the solvent was distilled off under reduced pressure. The residue was roughly purified by column chromatography (silica gel, hexane/ethyl acetate=1/1 (volume ratio)) to obtain Compound 7 (330 mg) as a mixture.

$^1$H NMR (400 MHz, CD$_3$OD) 1.79 (s, 3H), 1.82 (s, 3H), 6.15-6.16 (m, 3H), 6.76 (d, J=8.6 Hz, 2H), 7.04 (d, J=8.6 Hz, 2H); $^{13}$C NMR (125 MHz, CD$_3$OD) 22.7, 22.9, 101.5, 107.7, 115.9, 130.3, 133.4, 134.0, 136.9, 148.3, 156.8, 159.3; HRMS (FAB+): calcd for C$_{16}$H$_{17}$O$_3$ 257.1178, Found 257.1168 [M$^+$+H].

Step G: Production of 4-[3-(3,5-dimethoxyphenyl) but-2-en-2-yl]-1,2-dimethoxybenzene (8)

A suspension of Compound 5 (1.64 g, 5.15 mmol), 3,4-dimethoxyphenylboronic acid (1.41 g, 7.72 mmol), sodium carbonate (1.64 g, 15.4 mmol), and distilled water (5 mL) in DMF (25 mL) was stirred at room temperature for 15 minutes. Then, Pd(PPh$_3$)$_4$ (595 mg, 0.52 mmol) was added to the reaction mixture, followed by stirring at 90° C. for 19 hours. The reaction mixture was separated into layers using saturated saline and ethyl acetate, the organic layer was dried over anhydrous sodium sulfate, and the solvent was distilled off under reduced pressure. The residue was purified by column chromatography (silica gel) to obtain Compound (E)-8 (hexane/methylene chloride=2/1 (volume ratio), 870 mg, 52%, solid) and Compound (Z)-8 (hexane/methylene chloride/ethyl acetate=20/20/1 (volume ratio), 388 mg, 23%, solid).

(E)-8; $^1$H NMR (400 MHz, CDCl$_3$) 1.89 (s, 6H), 3.82 (s, 6H), 3.91 (s, 3H), 3.91 (s, 3H), 6.38 (t, J=2.4 Hz, 1H), 6.42 (d, J=2.4 Hz, 2H), 6.79-6.83 (m, 2H), 6.88 (d, J=8.0 Hz, 1H); $^{13}$C NMR (125 MHz, CDCl$_3$) 22.4, 22.6, 55.3, 55.9, 98.2, 106.3, 110.8, 111.6, 120.4, 132.6, 132.9, 136.9, 146.8, 147.4, 148.5, 160.6; FAB-MS m/z 329 (M$^+$+H).

(Z)-8; $^1$H NMR (400 MHz, CDCl$_3$) 2.14 (s, 3H), 2.15 (s, 3H), 3.58 (s, 3H), 3.59 (s, 6H), 3.80 (s, 3H), 6.15-6.17 (m, 3H), 6.47 (d, J=2.0 Hz), 6.63 (dd, J=8.0 and 2.0 Hz, 1H), 6.67 (d, J=8.0 Hz, 1H); $^{13}$C NMR (125 MHz, CDCl$_3$) 21.2, 21.3, 55.1, 55.6, 55.7, 97.9, 107.3, 1103, 113.0, 120.7, 132.4, 132.4, 137.2, 146.9, 147.0, 147.8, 160.1; FAB-MS m/z 329 (M$^+$+H).

Step H: Production of 4-[3-(3,5-dihydroxyphenyl) but-2-en-2-yl]benzene-1,2-diol (9)

A solution of Compound (E)-8 (183 mg, 0.56 mmol) in methylene chloride (5.6 mL) was cooled to −20° C. in an argon atmosphere, and boron tribromide (1.0 mol/L CH$_2$Cl$_2$ solution, 3.35 mL, 3.35 mmol) was added thereto dropwise, followed by stirring for 80 minutes. After further stirring at room temperature for 90 minutes, distilled water (50 mL) was added thereto. The reaction mixture was extracted with methylene chloride, and the water layer was further extracted with ethyl acetate. The obtained organic layers were combined, and the solvent was distilled off under reduced pressure. The residue was purified by HPLC (column: Shimadzu Shim Pack PRC-SIL (250×20 m); measurement wavelength: 254 nm; mobile phase: hexane/ethyl acetate=1/2 (volume ratio); flow rate: 20 mL/min) to obtain Compound 9 (Rt=4.2 min, 55 mg, 36%) as a solid.

$^1$H NMR (400 MHz, CD$_3$OD) 1.80 (s, 3H), 2.00 (s, 3H), 6.14 (br-s, 3H), 6.53 (dd, J=8.0 and 2.4 Hz, 1H), 6.65 (d, J=2.4 Hz, 1H), 6.74 (d, J==8.0 Hz, 1H); $^{13}$C NMR (125 MHz, CD$_3$OD) 20.9, 22.9, 101.4, 107.7, 116.1, 116.5, 120.7, 133.6, 133.8, 137.6, 144.7, 145.9, 159.3; FAB-MS m/z 273 (M$^+$+H). HRMS (FAB+): calcd for C$_{16}$H$_{17}$O$_4$ 273.1127, Found 273.1084 [M$^+$+H].

Example 2

Electron Spin Resonance (ESR) Measurement Test

Resveratrol (R), as well as dimethyl resveratrol (DR) and dimethylhydroxy resveratrol (DHR), which are compounds of the present invention, were added to radicals serving as standard substances, and the amounts of remaining tyrosine radicals and hydroxyl radicals were assessed. Specifically, a standard solution comprising a 50 mM NaPi buffer (pH 7.4), 10 mM DMPO, 1.6 mM myoglobin, and 1 mM H$_2$O$_2$ was prepared using myoglobin as a tyrosine radical. Further, a standard solution comprising a 50 mM NaPi buffer (pH 7.4), 10 mM DMPO, 0.1 mM Fe$^{2+}$-EDTA, and 1 mM H$_2$O$_2$ was prepared using Fe$^{2+}$-EDTA as a hydroxyl radical. Then, 5 µM, 50 µM, and 500 µM of resveratrol (R), dimethyl resveratrol (DR), and dimethylhydroxy resveratrol (DIR) were added to these standard solutions, and the amounts of tyrosine radicals and hydroxyl radicals were measured by electron spin resonance (ESR) using an ESR spectrometer RX-1 (produced by JEOL Ltd.) based on changes in absorption spectra. The ESR was set as follows: microwave power: 10 mW; adjusted frequency: 100 KHz; adjusted magnetic field: 0.1 G; receiver gain: 1000; and time constant: 0.3 s. FIGS. 1(A) and 1(B) show the results.

The results reveal that all of the compounds reduced radical generation in a concentration-dependent manner, and each showed a strong radical-generation reducing activity in the order of: resveratrol (R)<dimethyl resveratrol (DR) <dimethylhydroxy resveratrol (DHR).

Example 3

Therapeutic Efficacy Test Using Smoking Rat

Models of keratoconjunctival epithelial damage caused by dry eye were developed by the following method described in WO2012/161112, and the therapeutic effect of resveratrol (R), dimethyl resveratrol (DR), and dimethylhydroxy resveratrol (DHR) on the keratoconjunctival epithelial damage was evaluated.

In this experiment, both eyes of each animal were used. The same drug solution was administered to both eyes of each animal, and a comparison was made among groups.

Experimental Method

Six-week-old male Sprague-Dawley rats were subjected to smoking treatment to develop dry-eye, presbyopia models.

Specifically, a treatment in which mainstream smoke (300 mL) was added to a rat-containing chamber 6 times at 30-minute intervals was performed for 12 days to induce keratoconjunctival epithelial damage. As conditions for ocular instillation, a PBS solution of 300 µM resveratrol (R), dimethyl resveratrol (DR), or dimethylhydroxy resveratrol (DHR) was each instilled in the eyes daily for 11 days at one dose of 5 µL 4 times in total per day, i.e., once before the smoking treatment and 3 times after the treatment. Each group consisted of 4 animals (8 eyes).

After the 11-day smoking treatment, the body weight, tear volume, fluorescent staining score, and crystalline lens hardness were measured.

To determine the tear volume, tears accumulated in the cornea of rat were measured in accordance with the cotton thread test. Specifically, after the rats were anesthetized with ocular instillation of oxybuprocaine hydrochloride, a cotton thread was inserted between the palpebra and eyeball for 60 seconds, and tears were collected. The tear volume was assessed by measuring the length (mm) of the wet portion in the cotton thread.

After the completion of ocular instillation, a damaged portion in corneal epithelium was stained with a fluorescent dye (fluorescein). Then, the degree of corneal epithelial damage was assessed based on the following criteria by scoring each section of the entire cornea, which was divided into a total of 9 sections, i.e., upper, middle, and lower, and left, center, and right sections, and calculating the total value. Thereafter, the score values were compared among the groups for analysis. For statistical analysis, a significant difference test was performed by using the Dunnett method in terms of each group with respect to the smoking group. For unbiased evaluation, the content of the drug solution administered to each group was blinded from the initiation of ocular instillation to the scoring of the corneal epithelial damage, and collated after scoring.

Evaluation Criteria for Scoring of Fluorescein Staining of Corneal Epithelium

0: not stained (no punctate fluorescence)
1: weak punctate fluorescence
2: relatively intense punctate fluorescence
3: strong punctate fluorescence The crystalline lens hardness was measured by combining an electronic weighing scale and height gauge. A crystalline lens whose minor axis length had been previously measured was placed on an electronic weighing scale, and the weight was set to 0. The handle of a height gauge was used above the crystalline lens to allow the end portion to be in contact with the crystalline lens. Further using the handle, the end portion was lowered about 5 to 10% of the minor axis length to apply a pressure on the crystalline lens. The change in the weight at this time was measured with the electronic weighing scale, and the weight was divided by the moving distance measured with the height gauge. The resulting value was considered to be hardness. A larger value represents more hardness.

For statistical analysis of the body weight, tear volume, and crystalline lens hardness, a significant difference test was performed using the Dunnett method in terms of each group with respect to the smoking group.

Results

Figure 2:
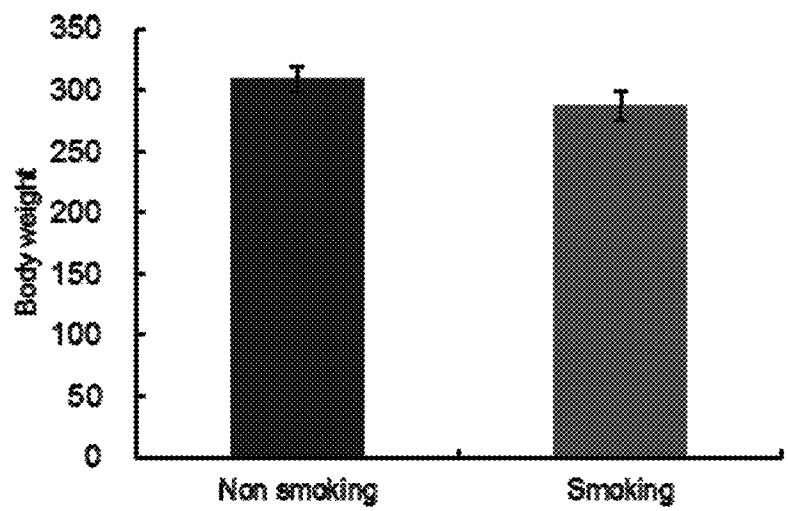
FIG. 2 is a graph showing the body weights of rats in the non-smoking group and smoking group.

Although there was no significant difference in the body weight, the body weight tended to decrease in the smoking group (Smoking), compared to the non-smoking group (Non-smoking) (FIG. 2). (The body weights of the non-smoking group and smoking group were respectively 308.2±10.4 g and 285.9±12.2 g.)

Figure 3:
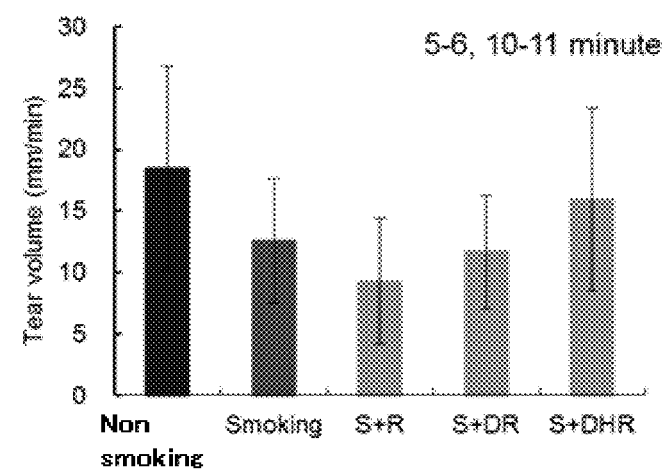
FIG. 3 is a graph showing average tear volumes 5 to 6 and 10 to 11 minutes after administration of drugs when various drugs were administered after smoking treatment. Non-smoking: without smoking treatment; Smoking: with smoking treatment; S+R: smoking treatment with resveratrol administration; S+DR: smoking treatment with dimethyl resveratrol administration; and S+DHR: smoking treatment with dimethylhydroxy resveratrol administration.

Although the tear volume was decreased by the smoking treatment, a tendency toward the improvement of the tear volume was observed when resveratrol, dimethyl resveratrol (DR), or dimethylhydroxy resveratrol (DHR) was added (FIG. 3). (The tear volumes of the non-smoking group, smoking group, R group, DR group, and DHR group were respectively 14.0±9.1 mm, 10.0±5.0 mm, 6.9±4.3 mm, 8.3±4.9 mm, and 13.8±11.1 mm.)

Figure 4:
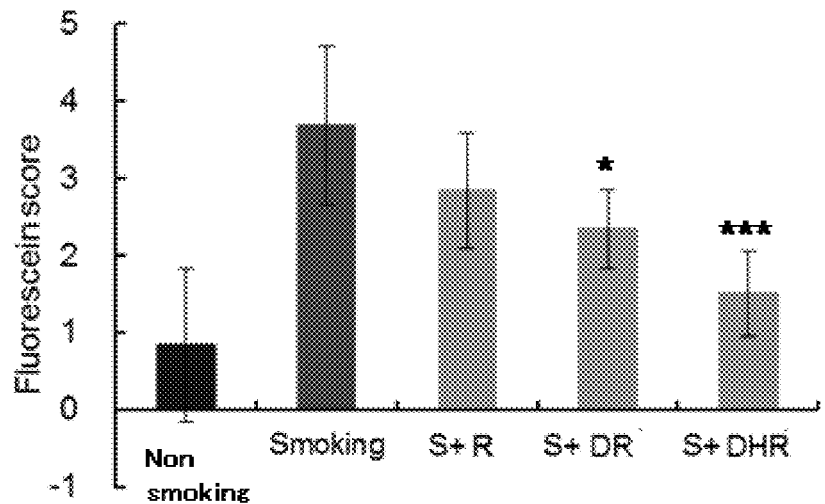
FIG. 4 is a graph showing fluorescent staining scores obtained when various drugs were administered.

The fluorescent staining score increased in the smoking group (average fluorescein score: 3.7±1.0), compared to the non-smoking group (average fluorescein score: 0.8±1.0); however, the score decreased with the drug administration (DR group (average fluorescein score: 2.3±0.5), $p<0.05$ with respect to the smoking group; and DHR group (average fluorescein score: 1.5±0.5), $p<0.005$ with respect to the smoking group), which confirmed that the ocular instillation of the drugs of the present invention improved the corneal state (FIG. 4)

As is clear from the results of the tear volume measurement and the results of fluorescent staining score, or from the results of fluorescent staining score, the drugs of the present invention are useful as a prophylactic and/or therapeutic agent for corneal and conjunctival diseases, such as dry eye, keratoconjunctivitis sicca, superficial punctate keratopathy, corneal erosion, or corneal ulcer.

Figure 5:
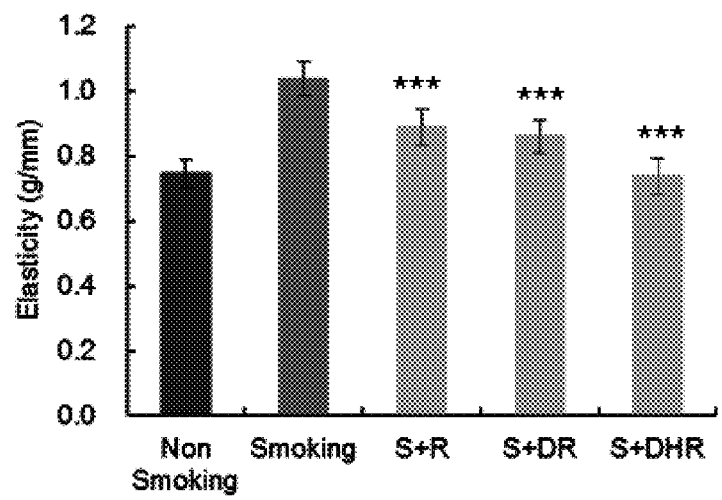
FIG. 5 is a graph showing elasticity of crystalline lens obtained when various drugs were administered.

The crystalline lens elasticity serves as an index of presbyopia because a crystalline lens becomes harder with aging. The elasticity was increased in the smoking group (1.04±0.05), compared to the non-smoking group (0.75±0.04); however, the elasticity was decreased with the drug administration (R group (elasticity: 0.87±0.06), $p<0.005$ with respect to the smoking group; DR group (elasticity: 0.86±0.06), $p<0.005$ with respect to the smoking group; and DHR group (elasticity: 0.75±0.05), $p<0.005$ with respect to the smoking group). Significant crystalline lens-hardening was observed, and the ocular instillation of the drugs of the present invention inhibited the crystalline lens-hardening (FIG. 5).

As is clear from the test result of crystalline lens elasticity, the drugs of the present invention are useful as a prophylactic and/or therapeutic agent of presbyopia.

Example 4

Measurement of Radical Scavenging Activity

Active oxygen, such as hydroxyl radicals and peroxyl radicals, has very high reactivity to antioxidants and various organic compounds, and has no absorption in the visible portion. For this reason, it is very difficult to perform kinetic analysis in terms of the radical scavenging ability of antioxidants. Unlike active oxygen, a galvinoxyl radical (GO•), which is a relatively stable organic oxygen radical having a characteristic peak absorption at 428 nm, may be used to perform kinetic analysis in terms of the radical scavenging ability of antioxidants using ultraviolet visible spectroscopy. In view of this, changes at 428 nm, i.e., a decrease in the peak at 428 nm due to the reaction of GO• with an antioxidant (resveratrol (R), dimethyl resveratrol (DR), or dimethylhydroxy resveratrol (DHR)) was subjected to kinetic analysis to thus determine the radical scavenging activity of these antioxidants. The measuring method of radical scavenging activity is disclosed in publicly known documents (K. Dukuhara, et al., Chem. Res. Toxicol, 21, 282-287 (2008); K. Imai, et al., Bioorg. Med. Chem. Lett., 24, 2582-2584 (2014)).

Reagent:

In this experiment, the radical scavenging rate was measured by a stopped flow method. The following reagent was used:

Acetonitrile (Nacalai Tesque, Inc., 00433-95); and
Galvinoxyl Radical (Aldrich, G30-7).

Measurement Method:

A solution of GO• in acetonitrile (about $2.4 \times 10^{-6}$ M) was bubbled with argon for 7 minutes to remove molecular oxygen. Further, antioxidants (resveratrol, dimethyl resveratrol, dimethylhydroxy resveratrol) were dissolved in acetonitrile to prepare solutions having 5 or more different concentrations within a range of $2.4 \times 10^{-5}$ M to $2.5 \times 10^{-3}$ M, which were bubbled with argon for 7 minutes to remove molecular oxygen. Subsequently, the acetonitrile solutions of GO• and the compounds were simultaneously mixed to measure changes in the peak absorption of GO• (at 428 nm) over time by a stopped flow method.

Analysis:

Under conditions in which the concentration of each antioxidant is 10 times or more than that of GO• ([Antioxidant agent]>10[GO•]), the reduction in the absorbance at 428 nm derived from GO• follows the pseudo-first-order kinetics (equation (1)) with respect to the concentration of each antioxidant agent (antioxidant):

$$-d[GO•]/dt = k_{obs}[GO•] \quad (1),$$

wherein "$k_{obs}$" is a pseudo-first-order kinetic constant. Integration of both sides of equation (1) leads to equation (2):

$$\ln([GO•]/[GO•]_0) = -k_{obs}t \quad (2),$$

wherein $[GO•]_0$ is a concentration of GO• when $t=0$.

If the absorbance at 428 nm at the time when $t=0$, $t$, or $\infty$ is $A_0$, $A_t$, or $A\infty$, respectively, then the relationship in equation (3) exists between the GO• concentration and absorbance, and equation (4) is obtained from equation (2) and equation (3):

$$[GO•]/[GO•]_0 = (A_t - A\infty)/(A_0 - A\infty) \quad (3)$$

$$\ln(A_t - A\infty) = -k_{obs}t + \ln(A_0 - A\infty) \quad (4)$$

According to equation (4), when $\ln(A_t - A\infty)$ is plotted with respect to time t, a straight line is obtained, and based on its slope, a pseudo-first-order kinetic constant $k_{obs}$ is obtained. In fact, a straight line was obtained when $\ln(A_t - A\infty)$ was plotted with respect to time t, and $k_{obs}$ was determined based on its slope. The obtained $k_{obs}$ increased in proportion to the increase in the concentration of the antioxidant.

Therefore, the relationship in equation (5) exists between $k_{obs}$ and the constant ($k_{HT}$) Of rate of hydrogen transfer from the antioxidants to GO•.

$$k_{obs} = k_{HT}[\text{antioxidant}] \quad (5)$$

Accordingly, the entire reaction rate is represented by equation (6), and it was clarified that it was a first-order reaction with respect to each concentration of GO• and the antioxidant agent.

$$\text{Rate} = d[GO•]/dt = k_{HT}[GO•][\text{antioxidants}] \quad (6)$$

The slope of the straight line in the graph in which the $k_{obs}$ was plotted on the vertical axis while each antioxidant was plotted on the horizontal axis (the constant ($k_{HT}$) of rate of hydrogen transfer to GO•) represents radical scavenging activity of each antioxidant. The radical scavenging activities of the antioxidants tested in these Examples were shown below. Dimethylhydroxy resveratrol had unexpectedly high radical scavenging activity, compared to resveratrol or dimethyl resveratrol.

Resveratrol: 4.1 $M^{-1} s^{-1}$
Dimethyl resveratrol: 0.96 $M^{-1} s^{-1}$
Dimethylhydroxy resveratrol: 2300 $M^{-1} s^{-1}$

Example 5

Therapeutic Efficacy Test Using Smoking Rat

Models of keratoconjunctival epithelial damage caused by dry eye were developed in accordance with the method described in Example 3, and the therapeutic effect of dimethyl resveratrol (DR) on the keratoconjunctival epithelial damage was compared with the therapeutic effect of a commercially available dry eye therapeutic agent, i.e., Diquas (registered trademark) Ophthalmic Solution 3% (Santen Pharmaceutical Co., Ltd., active ingredient: diquafosol sodium).

In this experiment, both eyes of each animal were used. The same drug solution was administered to both eyes of each animal, and a comparison was made among groups.

Six-week-old male Sprague-Dawley rats were subjected to smoking treatment to develop dry-eye models.

Specifically, a treatment in which mainstream smoke (300 mL) was added to a rat-containing chamber 6 times at 30-minute intervals was performed for 12 days to induce a keratoconjunctival epithelial damage. As conditions for ocular instillation, a solution of 300 μM dimethyl resveratrol (DR) in PBS or the Diquas ophthalmic solution 3% was each instilled in the eyes daily for 11 days at one dose of 5 μL 4 times in total per day, i.e., once before the smoking treatment and 3 times after the treatment. The non-smoking group (Non-smoking) consisted of 6 animals (12 eyes), and the smoking group (Smoking), the dimethyl resveratrol group (DR), and the diquafosol sodium (Diquafosol) group each consisted of 4 animals (8 eyes)

After the 11-day smoking treatment, the body weight, tear volume, and fluorescent staining score were measured.

The tear volume and fluorescent staining score were measured in accordance with the method described in Example 3.

For statistical analysis, a significant difference test was performed using the Dunnett method in terms of each group with respect to the smoking group.

Results

No significant difference was found in the body weights among the non-smoking group (Non-smoking), smoking group (Smoking), dimethyl resveratrol group, and diquafosol sodium group. (The body weights of the non-smoking group, smoking group, DR group, and diquafosol sodium group were respectively 281.6±7.4 g, 280.0±5.8 g, 271.0±7.5 g, and 273.8±4.3 g.)

Figure 6:
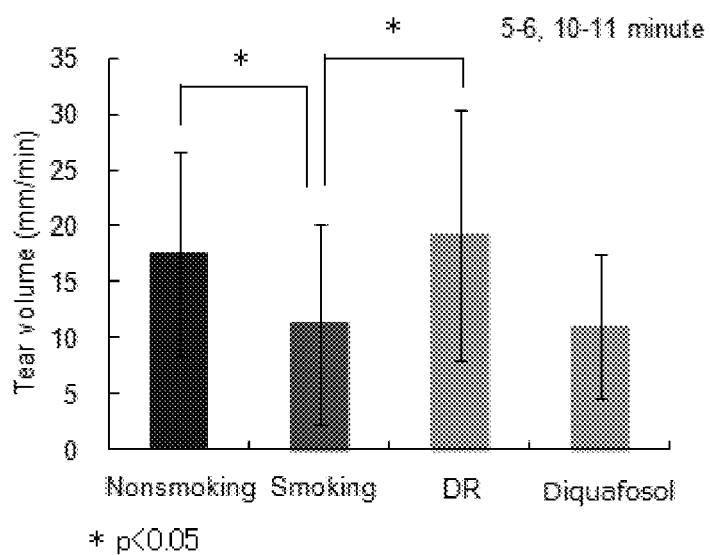
FIG. 6 is a graph showing average tear volumes 5 to 6 and 10 to 11 minutes after administration of drugs when various drugs were administered after smoking treatment. Non-smoking: without smoking treatment; Smoking: with smoking treatment; DR: smoking treatment with dimethyl resveratrol administration; and Diquafosol: with diquafosol sodium administration.

Although the tear volume was decreased by the smoking treatment, a tendency toward the improvement of the tear volume was observed when dimethyl resveratrol was added; however, the instillation of Diquas did not show an improving effect (FIG. 6). (The tear volumes of the non-smoking group, smoking group, DR group, and diquafosol sodium group were respectively 17.6±9.1 mm, 11.3±9.0 mm, 19.3±11.2 mm, and 11.0±6.5 mm.)

Figure 7:
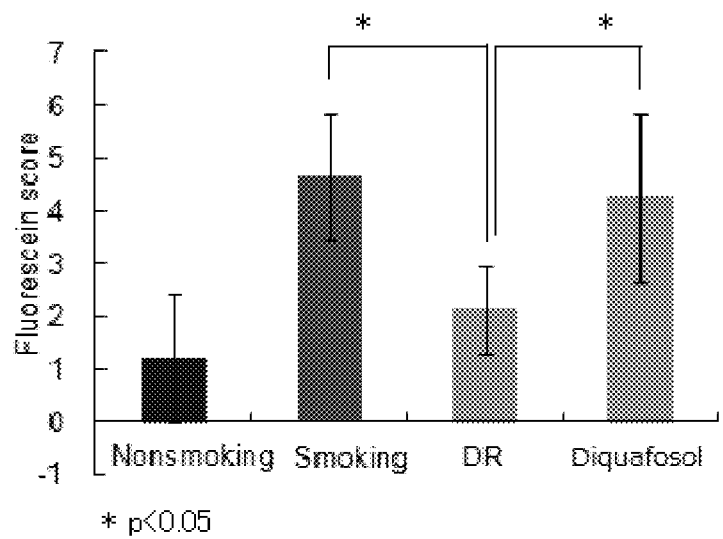
FIG. 7 is a graph showing fluorescent staining scores obtained when various drugs were administered.

The fluorescent staining score was increased in the smoking group (average fluorescein score: 4.6±1.2), compared to the non-smoking group (average fluorescein score: 1.2±1.2), and was significantly decreased with the administration of DR (DR group (average fluorescein score: 2.1±0.8, p<0.05 with respect to the smoking group)); however, an improvement tendency could not be observed in the diquafosol sodium group (average fluorescein score: 4.3±1.6) (FIG. 7). The instillation of dimethyl resveratrol significantly reduced the fluorescent staining score (p<0.05), compared to the instillation of diquafosol sodium.

As is clear from the results of the tear volume measurement and the results of fluorescent staining score, or from the results of fluorescent staining score, dimethyl resveratrol, i.e., a drug of the present invention, is useful as a prophylactic and/or therapeutic agent for corneal and conjunctival diseases, such as dry eye, keratoconjunctivitis sicca, superficial punctate keratopathy, corneal erosion, or corneal ulcer, compared to diquafosol sodium, which is a publicly known dry eye therapeutic agent.

Example 6

Safety Test of Drug of the Present Invention

Figure 8:
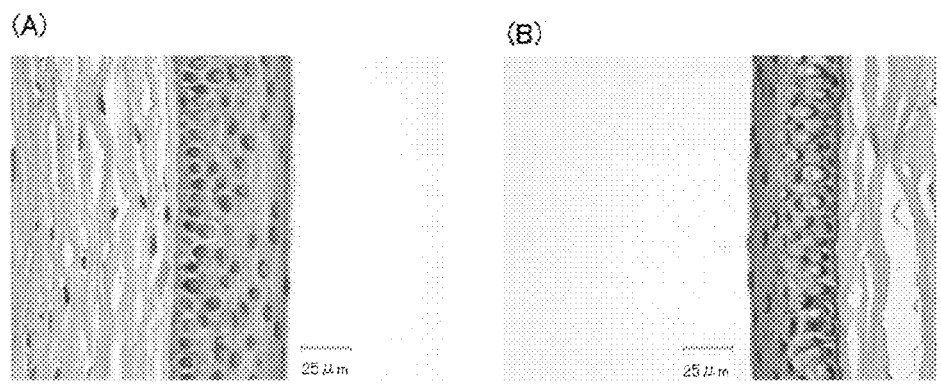
FIG. 8 is photographs of rat corneal tissue sections: (A) untreated; and (B) with the administration of the drug of the present invention. Magnification: 50×; and bar: 25 µm.

Hematoxylin-eosin staining was performed on the cornea of a rat that had been subjected to neither smoking treatment nor treatment using the drug, and the cornea of a rat that had been treated for one week with a drug of dimethyl resveratrol (300 µM PBS solution). FIGS. 8(A) and 8(B) show photographs of each tissue section.

According to the results, the instillation of dimethyl resveratrol did not show morphological effects on the corneal epithelium, which confirmed the safety in terms of a short-term administration of dimethyl resveratrol.

Example 7

Stability Test of Drug of the Present Invention

A solid of resveratrol, a solid of dimethyl resveratrol (DR), and 10 mM DMSO solutions (10% DMSO in water) were left to stand at 25° C. and 60% RH. After a constant period of time, the amount of each compound was measured by HPLC to evaluate the stability. The amount of the compound was calculated in accordance with:

(The amount of compound after a constant period of time)/(the amount of compound at the time when the test was initiated)×100(%).

Table 1 shows the results.

The solid of dimethyl resveratrol exhibited stability comparable to that of resveratrol. In the 10 mM DMSO solution, dimethyl resveratrol showed relatively high stability even one week later, and showed higher stability than that of resveratrol two weeks later.

TABLE 1

Stability Test of Resveratrol and DR

| | | Drug | | | | | | | | |
|---|---|---|---|---|---|---|---|---|---|---|
| | | Solid | | | | 10 mM Solution (10% DMSO in water) | | | | |
| Dosage Form | | 1 week | 2 weeks | 3 weeks | 4 weeks | 1 day | 2 days | 3 days | 1 week | 2 weeks |
| Resveratrol (%) | First time | 100 | 96 | 91 | 88 | 98 | 95 | 90 | 80 | 59 |
| | Second time | 101 | 96 | 90 | 86 | 99 | 96 | 90 | 82 | 65 |
| | Third time | 97 | 94 | 92 | 85 | 96 | 95 | 93 | 85 | 68 |
| | Average | 99 | 95 | 91 | 86 | 98 | 95 | 91 | 82 | 64 |
| DR (%) | First time | 98 | 98 | 97 | 94 | 99 | 96 | 94 | 85 | 72 |
| | Second time | 100 | 98 | 97 | 93 | 97 | 95 | 92 | 89 | 76 |
| | Third time | 99 | 97 | 95 | 94 | 100 | 98 | 96 | 90 | 81 |
| | Average | 99 | 98 | 96 | 94 | 99 | 96 | 94 | 88 | 76 |

The invention claimed is:

1. A method for treating a corneal and conjunctival disease or presbyopia, comprising administering to a patient an effective amount of a compound represented by Formula (I), or a salt thereof or a prodrug thereof,

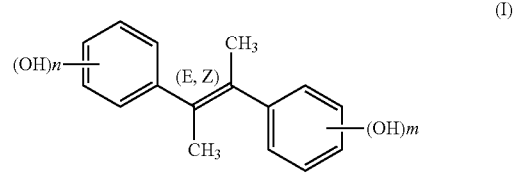

(I)

wherein m and n are each independently an integer of 0 to 5; m+n≥1; and each aromatic ring of the compound represented by Formula (I) may be substituted, thereby treating the corneal and conjunctival disease or presbyopia in the patient.

2. The method of claim 1, wherein m and n are each independently an integer of 1 to 3.

3. The method of claim 2, wherein the compound is a compound represented by Formula (II), or a salt thereof or a prodrug thereof,

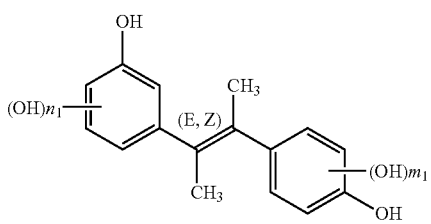

wherein $m_1$ and $n_1$ are each independently an integer of 0 to 2.

4. The method of claim 3, wherein the compound is a compound represented by Formula (III), or a salt thereof or a prodrug thereof,

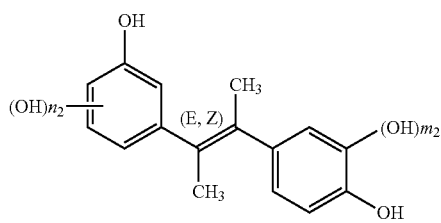

wherein $m_2$ is 0 or 1, and $n_2$ is an integer of 0 to 2.

5. A method for preventing a corneal and conjunctival disease or presbyopia, comprising administering to a patient an effective amount of a compound represented by Formula (I), or a salt thereof or a prodrug thereof,

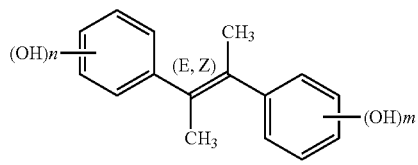

wherein m and n are each independently an integer of 0 to 5; $m+n \geq 1$; and each aromatic ring of the compound represented by Formula (I) may be substituted, thereby preventing the corneal and conjunctival disease or presbyopia in the patient.

6. The method of claim 5, wherein m and n are each independently an integer of 1 to 3.

7. The method of claim 6, wherein the compound is a compound represented by Formula (II), or a salt thereof or a prodrug thereof,

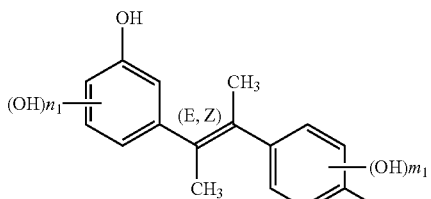

wherein $m_1$ and $n_1$ are each independently an integer of 0 to 2.

8. The method of claim 7, wherein the compound is a compound represented by Formula (III), or a salt thereof or a prodrug thereof,

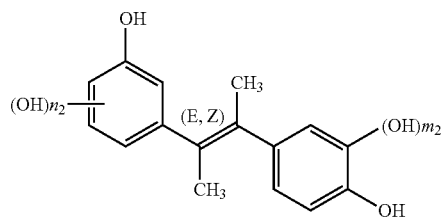

wherein $m_2$ is 0 or 1, and $n_2$ is an integer of 0 to 2.

9. The method of claim 1, wherein the compound represented by Formula (I), or a salt thereof or a prodrug thereof, is in a pharmaceutical composition further comprising a pharmaceutically acceptable carrier.

10. The method of claim 9, wherein m and n are each independently an integer of 1 to 3.

11. The method of claim 10, wherein the compound is a compound represented by Formula (II), or a salt thereof or a prodrug thereof,

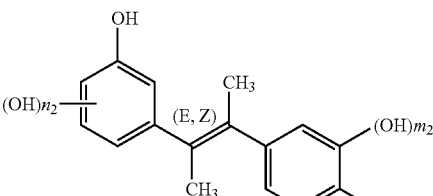

wherein $m_1$ and $n_1$ are each independently an integer of 0 to 2.

12. The method of claim 11, wherein the compound is a compound represented by Formula (III), or a salt thereof or a prodrug thereof,

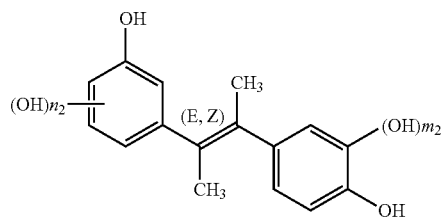

wherein $m_2$ is 0 or 1, and $n_2$ is an integer of 0 to 2.

* * * * *